United States Patent
Fayyaz et al.

(10) Patent No.: US 10,405,972 B2
(45) Date of Patent: Sep. 10, 2019

(54) SYSTEMS AND METHODS FOR INTRAOCULAR LENS DEPLOYMENT

(71) Applicant: NOVARTIS AG, Basel (CH)

(72) Inventors: Asif Fayyaz, Euless, TX (US); Jian Liu, Arlington, TX (US); Sudarshan B. Singh, Euless, TX (US); Chris Belisle, Somerset, WI (US); Bill Hartsig, Hudson, WI (US); Sam Jang, Woodbury, MN (US); Tyler Buchanan, Chippewa Falls, WI (US); Aaron Munsinger, Elk Mound, WI (US)

(73) Assignee: Novartis AG, Basel (CH)

(*) Notice: Subject to any disclaimer, the term of this patent is extended or adjusted under 35 U.S.C. 154(b) by 279 days.

(21) Appl. No.: 15/238,547

(22) Filed: Aug. 16, 2016

(65) Prior Publication Data
US 2017/0367816 A1 Dec. 28, 2017

Related U.S. Application Data

(60) Provisional application No. 62/354,015, filed on Jun. 23, 2016.

(51) Int. Cl.
*A61F 2/16* (2006.01)

(52) U.S. Cl.
CPC .......... *A61F 2/1672* (2013.01); *A61F 2/1667* (2013.01)

(58) Field of Classification Search
CPC ...... A61F 2/1667; A61F 2/1672; A61F 2/167; A61F 2/1662; A61F 2/1664; A61B 5/15117; A61B 17/3468
See application file for complete search history.

(56) References Cited

U.S. PATENT DOCUMENTS

| | | | | |
|---|---|---|---|---|
| 5,881,942 | A | * 3/1999 | Bergamini | ................ B25C 1/02 227/129 |
| 2014/0257315 | A1 | * 9/2014 | Wu | ......................... A61F 2/167 606/107 |
| 2014/0257317 | A1 | * 9/2014 | Safabash | ............... A61F 2/1678 606/107 |

* cited by examiner

*Primary Examiner* — Diane D Yabut
*Assistant Examiner* — Majid Jamialahmadi

(57) ABSTRACT

An intraocular lens (IOL) insertion apparatus may include a handpiece body having a distal tip and a deployment chamber located at a distal end of the handpiece body. The deployment chamber is sized and shaped to hold a folded IOL. The IOL insertion apparatus further includes a deployment system disposed within the handpiece body. The deployment system may include a deployment carriage movable between a first position and a second position within the handpiece body. The deployment carriage may include a biasing element that biases the deployment carriage in a distal direction toward the distal tip. The deployment system may further include a deployment trigger that prevents distal movement of the deployment carriage unless pressed and a deployment plunger having a proximal end secured to the deployment carriage and a distal end to engage the folded IOL.

19 Claims, 6 Drawing Sheets

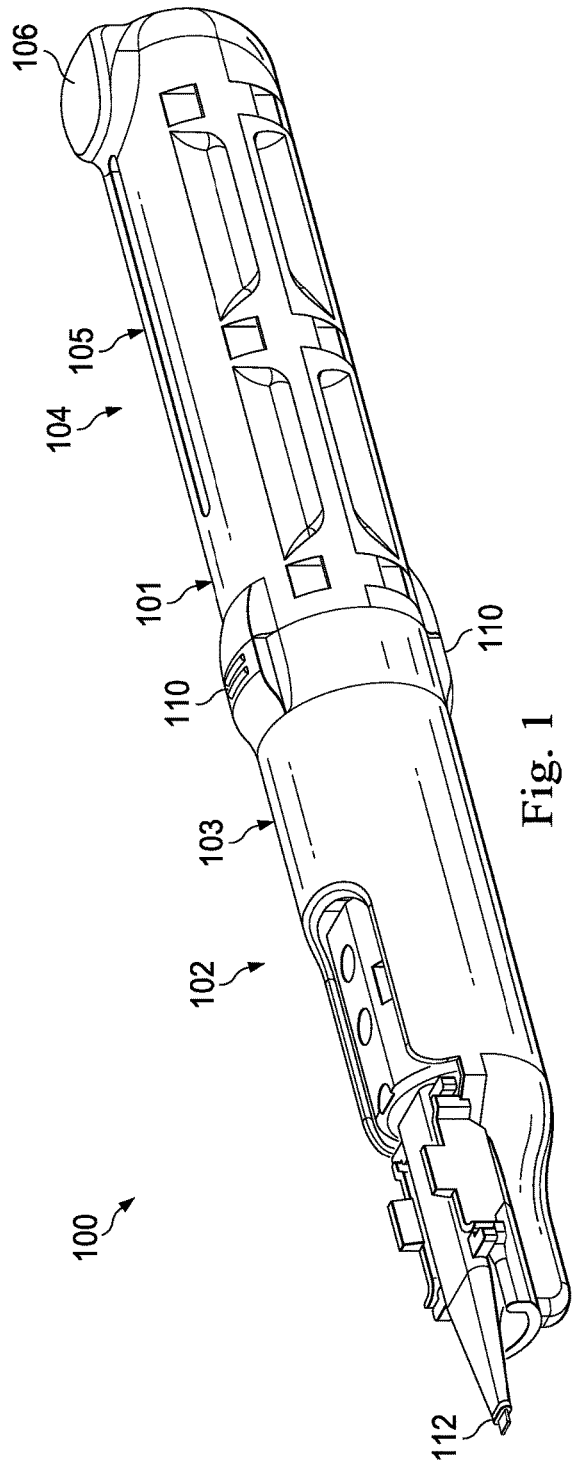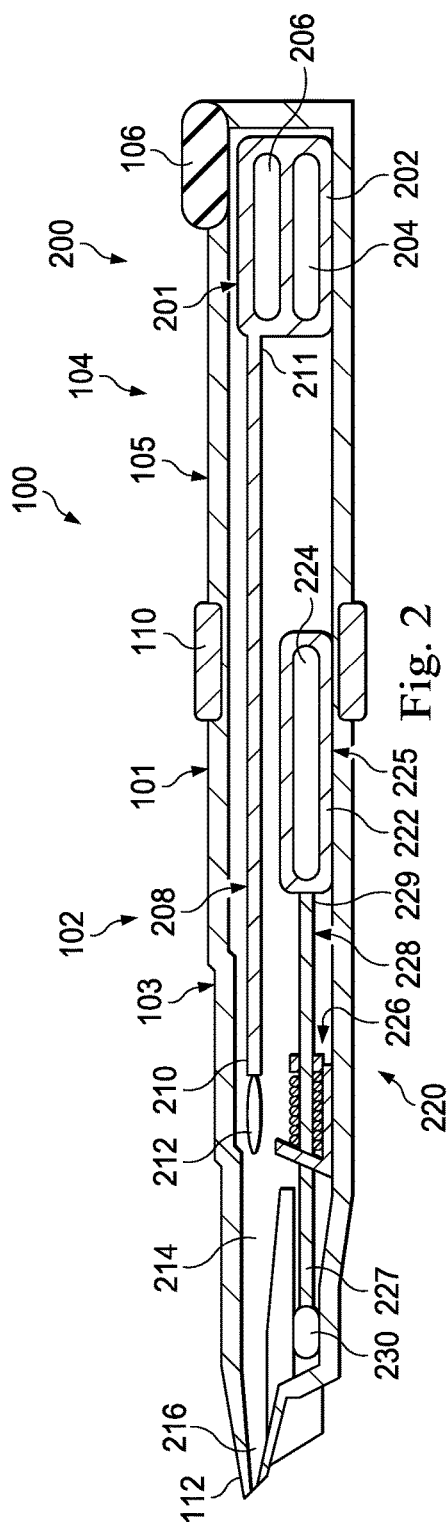

SYSTEMS AND METHODS FOR INTRAOCULAR LENS DEPLOYMENT

CROSS-REFERENCE TO RELATED APPLICATIONS

This application claims the benefit of U.S. Provisional Application No. 62/354,015, filed Jun. 23, 2016, the entire contents of which are incorporated herein by reference.

TECHNICAL FIELD

The present disclosure is directed to methods and systems for performing ophthalmic surgical procedures, and more particularly, to methods and systems for advancing an intraocular lens for an ophthalmic surgical procedure.

BACKGROUND

The human eye, in simple terms, functions to provide vision by refracting light passing through a clear outer portion called the cornea and focusing the light by way of the lens onto the retina at the back of the eye. The quality of the visual image created by the focused light depends on many factors including the size, shape, and length of the eye, and the shape and transparency of the cornea and lens.

When trauma, age, or disease causes the lens to become less transparent, vision deteriorates because of a reduction in light transmitted to the retina. This deficiency in the eye's lens is medically known as a cataract. The treatment for this condition is often surgical removal of the natural lens and implantation of an artificial lens, typically termed an Intraocular Lens (IOL).

Insertion of an IOL is typically performed using an IOL insertion tool. A conventional IOL insertion tool includes an IOL insertion cartridge that may fold and insert the IOL through a relatively small incision into the eye. For example, the IOL cartridge may include a folding chamber that has walls shaped to cause the IOL to fold as desired as the IOL is moved through the chamber. Then, the folded IOL may be deployed into the patient's eye through the small incision. Typically, the operator of the IOL insertion tool manually pushes a fold-plunger that advances the IOL through the folding chamber. The operator also manually pushes the plunger to advance the IOL out of the distal end of the IOL insertion tool and into the patient's eye. However, since the manual force applied to the plunger may vary by use and by operator, the appropriate folding forces may not be achieved in some instances. This can lead to undesirable folding results. Furthermore, the manual force applied to advance the IOL into the patient's eye may vary by use and by operator, leading to inconsistent surgical outcomes. It is desirable to find methods and systems for providing improved and consistent advancement of the IOL through the folding chamber and deployment of the IOL into the patient's eye.

SUMMARY

An intraocular lens (IOL) insertion apparatus may include a handpiece body having a distal tip and a deployment chamber located at a distal end of the handpiece body. The deployment chamber is sized and shaped to hold a folded IOL. The IOL insertion apparatus further includes a deployment system disposed within the handpiece body. The deployment system may include a deployment carriage movable between a first position and a second position within the handpiece body. The deployment carriage may include a biasing element that biases the deployment carriage in a distal direction toward the distal tip. The deployment system may further include a deployment trigger that prevents distal movement of the deployment carriage unless pressed and a deployment plunger having a proximal end secured to the deployment carriage and a distal end to engage the folded IOL.

An advancement system may be disposed within the handpiece body. The advancement system may include an advancement carriage located within the handpiece body at a location proximal of the deployment carriage and an elongated advancement plunger having a distal end arranged to engage the IOL and a proximal end connected to the advancement carriage. The advancement carriage may include a biasing element that biases the advancement carriage in the distal direction toward the deployment carriage. The advancement carriage may also include a dampening system to dampen motion of the advancement carriage. The advancement carriage may be operative to abut against the deployment carriage after moving in the distal direction. The biasing element of the advancement carriage and the biasing element of the deployment carriage together may provide a force to push the IOL out of the distal tip. An advancement trigger may release the advancement carriage to move in the distal direction. The deployment trigger may include a spring-loaded cleat. The cleat may include a through-hole, and the deployment plunger may extend through the through-hole. When the deployment trigger is in an unengaged state, the cleat may grasp the deployment plunger with a surface of the through-hole to prevent distal movement of the deployment carriage. Engagement of the deployment trigger may change an angle of the through-hole to allow the deployment plunger to slide through the through-hole. The handpiece body may include a distal section and a proximal section. The proximal section may be slidingly engaged and rotatable from a first rotational position to a second rotational position relative to the distal section when proximally displaced from the distal section. When the proximal section is at the first rotational position relative to the distal section, an advancement plunger may be aligned with the IOL, and, when the proximal section is at the second rotational position relative to the distal section, the deployment plunger may be aligned with the IOL. The deployment trigger may be inaccessible to an operator until the proximal section is at the second rotational position with respect to the distal section. The biasing element of the deployment carriage comprises a constant force spring.

An intraocular lens (IOL) insertion apparatus may include a handpiece body having a proximal section and a distal section, the distal section having a distal tip, the distal section being rotatable relative to the proximal section between a first rotational position and a second rotational position, the first rotational position aligning an advancement plunger with an IOL positioned within the handpiece body, and the second rotational position aligning a deployment plunger with the IOL. The IOL insertion apparatus may further include a deployment carriage connected to a proximal end of the deployment plunger and releasably secured at a first position within the handpiece body by a deployment trigger, the deployment carriage comprising a first biasing element that biases the deployment carriage in a distal direction toward the distal tip. The IOL insertion apparatus may further include an advancement carriage connected to a proximal end of the advancement plunger and releasably secured within the handpiece body by an advancement trigger mechanism, the advancement carriage comprising a second biasing element to bias the advancement carriage in the distal direction.

The advancement carriage may be operative to abut against the deployment carriage after moving in the distal direction. The deployment trigger may grip the deployment plunger to prevent distal movement of the deployment carriage. When the deployment trigger is pressed, the deployment carriage may move the deployment plunger in the distal direction. The deployment trigger may be inaccessible until the distal section is at the second rotational position relative to the proximal section.

A method may include positioning a distal end of an intraocular lens (IOL) insertion apparatus handpiece at a surgical site. The method may further include triggering an advancement trigger mechanism that releases an advancement carriage, the advancement carriage having an advancement plunger extending from a distal end, the advancement carriage being biased in a distal direction such that when released, the advancement moves a distal tip of the advancement plunger through a folding chamber to fold an IOL engaged with the distal tip. The method may further include rotating a proximal section of the handpiece with respect to a distal section of the handpiece to align a deployment plunger with the folded IOL and actuating a deployment trigger to release a deployment carriage, the deployment carriage having a deployment plunger extending from a distal end, the deployment carriage being biased in the distal direction such that when the deployment trigger is actuated, the deployment carriage causes the deployment plunger to move the folded IOL out of the IOL insertion apparatus.

The proximal section may be moved away from the distal section before rotating the proximal section. The proximal section may be moved towards the distal section after rotating the proximal section.

BRIEF DESCRIPTION OF THE DRAWINGS

The accompanying drawings illustrate embodiments of the devices and methods disclosed herein and together with the description, serve to explain the principles of the present disclosure.

FIG. 1 is a diagram showing an illustrative intra-ocular lens (IOL) insertion apparatus that provides automated deployment of an IOL.

FIG. 2 is a diagram showing a cross-sectional view of a portion of the IOL insertion apparatus that provides automated deployment of the IOL.

DETAILED DESCRIPTION

Figure 3:
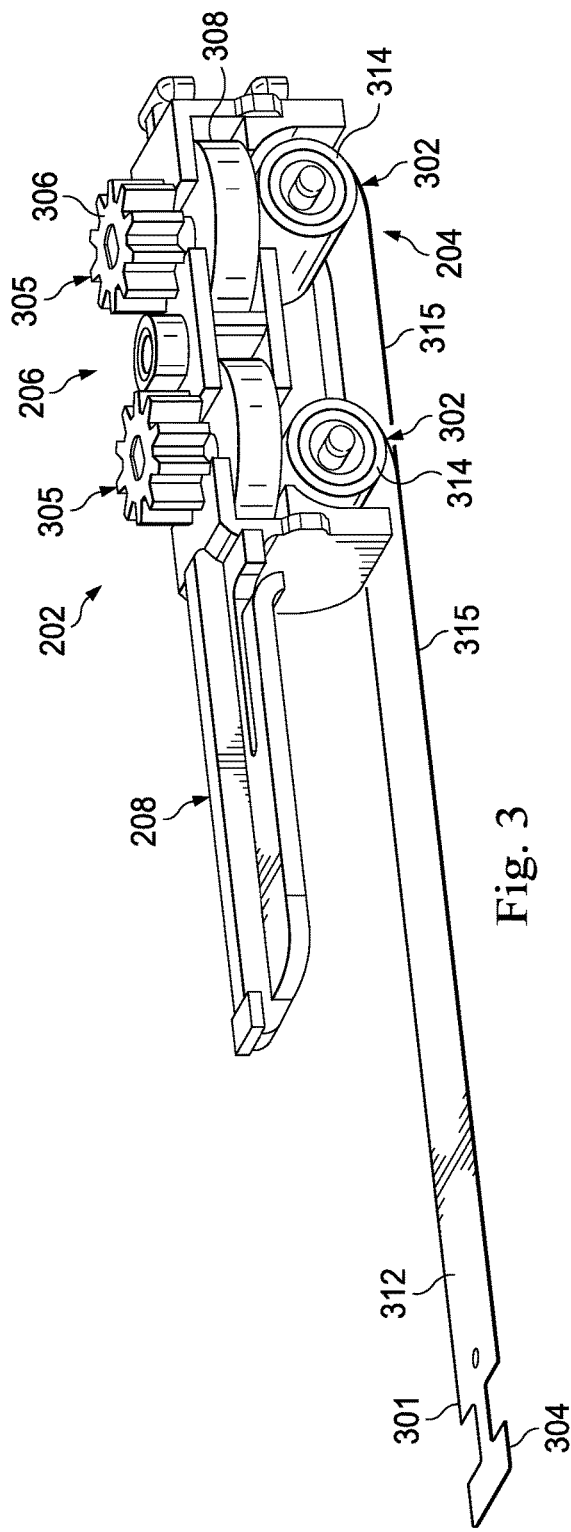
FIG. 3 is a perspective view of an illustrative advancement carriage for use in the IOL insertion apparatus.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

According to principles described herein, IOL insertion apparatuses may employ automated IOL deployment systems that inject an IOL into a patient's eye. Some implementations also include automated advancement of the IOL through the folding chamber. The automated IOL deployment system may apply a consistent, predictable force on a plunger, irrespective of the operator. This may result in a higher percentage of properly inserted lenses than can be obtained with conventional systems. Furthermore, the automated IOL deployment system may be self-contained within the IOL insertion tool, without relying upon any external powering mechanism.

In some examples of principles described herein, an IOL insertion apparatus includes a hand-piece body that includes a deployment chamber positioned distal of a folding chamber. The deployment chamber may hold a folded IOL, ready for deployment or injection into the eye. A deployment carriage, carrying a deployment plunger, may be releasably secured at a first position within the hand-piece body. The deployment plunger may engage and advance a folded IOL out of the deployment chamber and into a patient's eye. In some implementations, the deployment carriage may be spring-biased in the distal direction such that when a deployment trigger is engaged, the deployment carriage moves in a distal direction from the first position to a second position, thereby causing the deployment plunger to move the IOL out of the deployment chamber and into the patient's eye. An operator of the IOL insertion apparatus may halt the distal movement of the deployment carriage during its advancement by releasing the deployment trigger. The IOL insertion apparatus with automated advancement of the IOL will be described in further detail below.

FIG. 1 is a diagram showing an illustrative IOL insertion apparatus that provides automated deployment of an IOL. According to the present example, the IOL insertion apparatus 100 includes a handpiece body 101 having a distal section 102 with a distal tip 112 and having a proximal section 104. The distal section 102 includes a distal body 103 and the proximal section 104 includes a proximal body 105. The IOL insertion apparatus 100 also includes a set of release tabs 110 and includes an advancement trigger 106.

The handpiece body 101 is arranged to be gripped by an operator such as a surgeon. Thus, the handpiece body 101 may be ergonomically shaped for gripping by hand. In some examples, the IOL insertion apparatus may be a single-use device that may be discarded after the IOL within the IOL insertion apparatus has been inserted into the patient's eye.

The advancement trigger 106 may be used to initiate movement of the IOL through the folding chamber to fold the IOL. In this particular example, the advancement trigger 106 is a release button. In some examples, the advancement process, which includes advancement of the IOL through the folding chamber, may be automated. In such an example, an operator may trigger the folding process by, for example, pressing the release button 106.

The release tabs 110 may be used to release the proximal section 104 from the distal section 102. As will be described in further detail below, the proximal section 104 may be moved a predefined distance away from the distal section 102, rotated approximately 180 degrees about a longitudinal axis 650 of the IOL insertion apparatus 100, and then moved back towards the distal section 102. This motion prepares the IOL insertion apparatus 100 for the deployment process after the advancement process is completed. The deployment process involves ejecting the IOL out of the distal tip 112 of the IOL insertion apparatus 100 and into the patient's eye.

FIG. 2 is a diagram showing a cross-sectional view of a portion of the IOL insertion apparatus 100 that provides automated advancement and deployment of the IOL. The cross-sectional view illustrates an advancement system 200 that includes an advancement carriage 202 and an advancement plunger 208. The cross-sectional view also shows a deployment system 220 that includes a deployment carriage 222 and a deployment plunger 228. The cross-sectional view also shows an IOL 212, a folding chamber 214, and a deployment chamber 216. The advancement system 200 advances the IOL through the folding chamber 214 to the deployment chamber 216, and the deployment system 220 ejects the IOL from the deployment chamber and into the eye.

According to the present example, the advancement carriage 202 is secured at a proximal position 201 within the handpiece body 101. The advancement carriage 202 includes a spring system 204 and a dampening system 206. The spring system 204 may bias the advancement carriage 202 in a direction toward the distal tip 112 of the IOL insertion apparatus 100. The advancement carriage 202 may remain at the proximal position 201 until it is released from that position when an operator uses the advancement trigger 106. Upon release, the advancement carriage 202 moves in a distal direction, advancing the IOL 212 through the folding chamber 214. The distal movement of the advancement carriage 202 may be driven by the biasing spring system 204, while the rate of movement may be regulated or controlled by the dampening system 206.

Distal motion of the advancement carriage 202 may cause corresponding distal motion of the advancement plunger 208. The advancement plunger 208 is an elongated structure that has a proximal end 211 secured to the advancement carriage 202. The advancement plunger 208 has a distal end 210 that is configured to engage the IOL 212. The advancement plunger 208 may be supported and guided in its movement by a number of support and guidance structures (not shown), such as tracks, guides, or other features that may be carried by or formed as a part of the handpiece body 101.

In some implementations, the distal end 210, also referred to as the "tip" of the advancement plunger 208 may be substantially rigid in a manner permitting effective engagement with the IOL 212 to push the IOL 212 through the folding chamber 214. After the IOL 212 passes through the folding chamber 214, the IOL 212 may advance into the deployment chamber 216 near the distal end 112. The deployment chamber 216 may be shaped to narrow toward its distal end in a manner that may further compress the IOL 212 for passage through the incision in the eye. However, in some implementations, because the rigid tip 210 of the advancement plunger 208 is not compressible, it may not be able to extend into the narrowing region of the deployment chamber 216. As such, in some implementations, the deployment plunger 228 is then used to further advance and ultimately deploy the IOL in the eye.

According to the present example, the deployment carriage 222 is secured within the handpiece body at a first position 225 distal of the advancement carriage 202. The deployment plunger 228 may be attached to the deployment carriage 222. The deployment plunger 228 may be an elongated structure that has a proximal end 229 connected to the deployment carriage 222 and a distal end 227 having a compressible tip 230. FIG. 2 illustrates the advancement plunger 208 positioned to engage the IOL. However, as will be described in further detail below, the IOL insertion apparatus 100 can be configured such that the deployment plunger 228 is positioned to engage the IOL 212. When the deployment plunger 228 is positioned to engage the IOL 212, engaging the deployment trigger 226 causes the deployment plunger 228 to move in the distal direction to push the IOL 212 out of the distal tip 112.

The deployment carriage 222 includes a biasing system such as a spring system 224 that may bias the deployment carriage 222 towards the distal tip 112 of the IOL insertion apparatus 100. The deployment carriage 222 may remain at the first position 225 until it is released from that position when an operator uses the deployment trigger 226. In some examples, the deployment trigger 226 may be positioned on the handpiece housing 101 so as to be inaccessible to a user when the advancement plunger 208 is engaged with the IOL. However, the deployment trigger 226 may become accessible only after deployment plunger 228 is positioned to engage the IOL 212. Upon engagement of the deployment trigger 226, the spring system 224 may move the deployment carriage 222 forward in a distal direction toward the distal tip 112. The deployment carriage 222 may move forward until reaching a hard stop or until the operator discontinues engaging the deployment trigger 226. Forward movement of the deployment carriage 222 causes corresponding movement of the deployment plunger 228. As will be described in further detail below, forward movement of the deployment plunger 228 moves the IOL 212 out of the deployment chamber 216 and out of the distal tip 112 into the patient's eye.

In some implementations, the deployment plunger 228 has a tip 230 made of a compressible material. Thus, as the deployment plunger 228 engages the IOL 212, the tip 230 may compress to pass through the narrowing region of the deployment chamber 216 so as to move the IOL 212 out of the IOL insertion apparatus 100 and into the patient's eye.

FIG. 3 is a perspective view of an illustrative advancement carriage 202 for use in the IOL insertion apparatus (e.g., IOL insertion apparatus 100 shown in FIG. 1). As described above, the advancement carriage 202 may include the spring system 204 and the dampening system 206. In the present example, the spring system 204 includes one or more biasing elements such as constant force springs 302. A constant force spring is one in which the force applied by the spring remains constant despite the position of the spring. In other words, a constant force spring does not follow Hooke's law.

In the present example, each of the constant force springs 302 includes a coil 314 having an unrolled portion 315, a pickup portion 312 distal of the unrolled portion 315, and a mounting tab 304 at a distal end 301. In one example, the coils 314 include rolled-up, elongated metal sheets 311. The sheets 311 may be biased to the rolled-up position. Thus, when the sheets 311 are unrolled or extended as represented by the unrolled portion 315, the sheets 311 are biased to revert back to a rolled-up state absent any structure or force preventing the sheets 311 from doing so. The mounting tab 304 (only one is visible in FIG. 3) may be disposed at the distal end 301 and may be structurally configured to be secured to an interior of the handpiece body 101. The pickup portion 312 may be a portion of the sheet 311 disposed between the distal end 301 and the unrolled portion 315 and may not have spring-like properties. The pickup portion 312 may provide for ease of assembly and may maintain a substantially flat profile within a space between the advancement carriage 202 and a location to which the mounting tab 304 is secured. When the advancement carriage 202 is released, the unrolled portion 315 rolls-up to form a part of the coil 314 of the constant force spring 302, thus moving the advancement carriage 202 in the distal direction toward the mounting tab 304. While the present example illustrates only two constant force springs 302, other embodiments may include only one constant force spring or more than two constant force springs. In this example, the pickup portions 312 of the constant force springs 302 overlap each other and the constant force springs 302 cooperate together to bias the advancement carriage 202 toward the mounting tab 304 and toward the distal tip 112 of the IOL insertion apparatus.

The dampening system 206 helps control the speed of the distal movement of the advancement carriage 202 after the advancement carriage 202 has been released. In other words, the dampening system 206 prevents the advancement carriage from moving too fast once released by the advancement trigger (e.g., advancement trigger 106 shown in FIG. 1). In the present example, the dampening system 206 includes a plurality of rotary dampers 305. The rotary dampers 305 may include an injection molded body 308 and a pinion 306. The body 308 may include a viscous fluid, a rotor (not shown), and a stator (not shown). The rotary damper 305 may provide fluid damping through the shearing force of the fluid resistance between the surfaces of the rotor and stator. In this implementation, the pinion 306 includes a number of teeth that are configured to engage a rack (not shown) that may extend along an inner surface of the handpiece body 101. As such, when the advancement carriage 202 advances, the rack rotates the pinions, which in turn rotates the rotor in the viscous fluid in the body 308, thereby dampening the forward movement of the advancement carriage 202. While the present example illustrates two rotary dampers 305, other implementations may include a single rotary damper or more than two rotary dampers.

Figure 4:
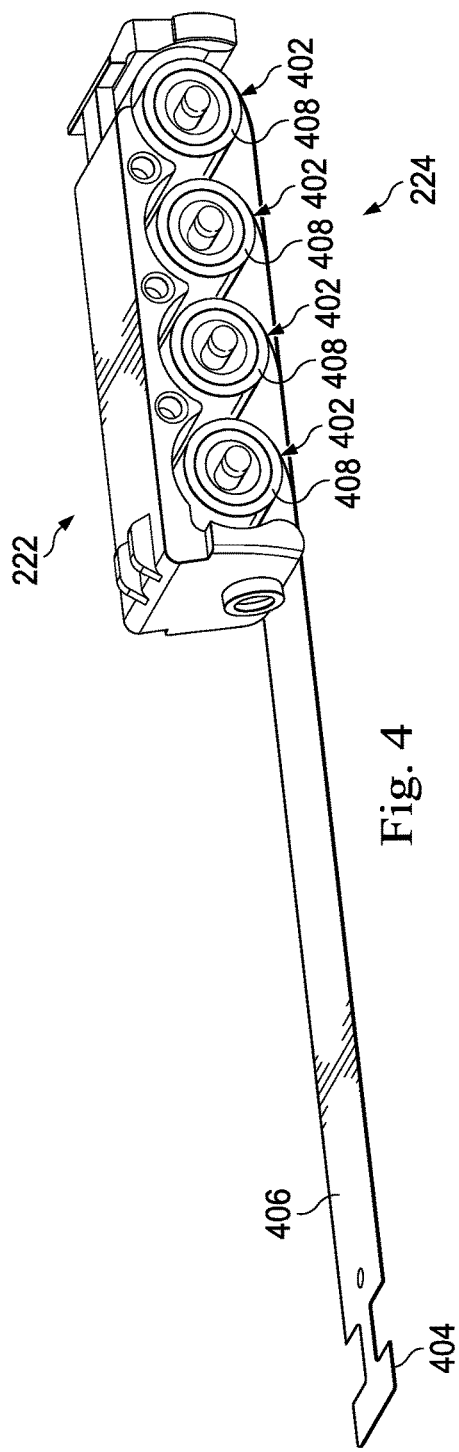
FIG. 4 is a perspective view of an illustrative deployment carriage for use in the IOL insertion apparatus.

FIG. 4 is a perspective view of an illustrative deployment carriage 222 for use in the IOL insertion apparatus. According to the present example, the spring system 224 of the deployment carriage 222 includes four constant force springs 402. Some implementations, however, may include fewer or more than four constant force springs. Like the constant force springs 302 described above, the constant force springs 402 include a coil 408, a pickup portion 406, and a mounting tab 404. In this example, the pickup portions 406 of the constant force springs 402 overlap each other and the constant force springs 402 cooperate together to bias the deployment carriage toward the mounting tab 404 and toward the distal tip 112 of the IOL insertion apparatus.

Figure 5A:
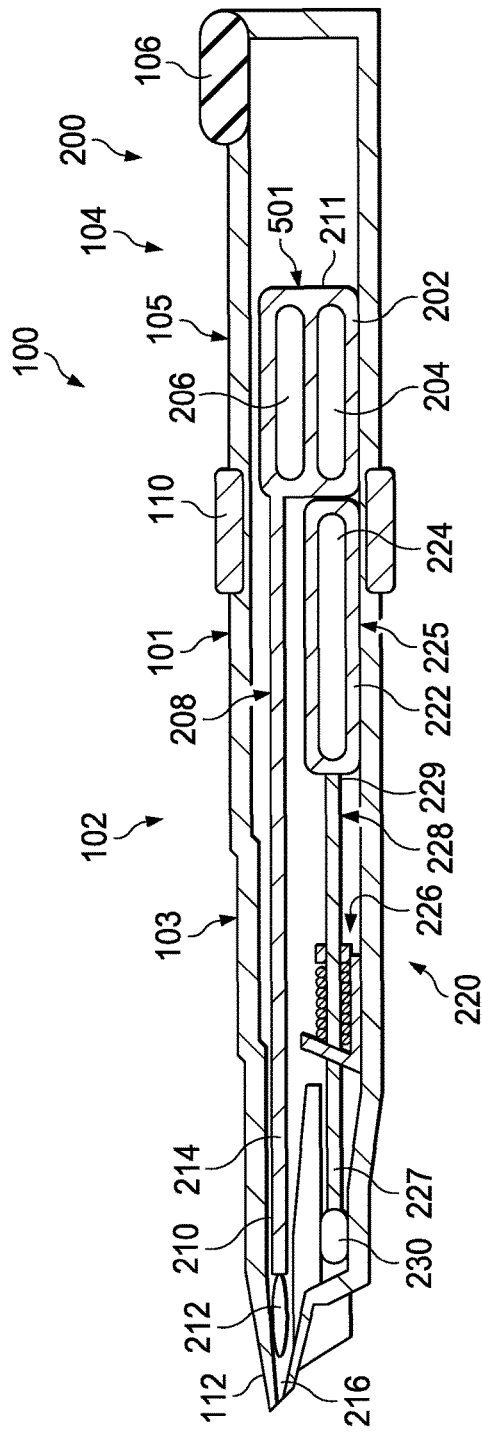
FIG. 5A is a diagram showing a cross-sectional view of the IOL insertion apparatus with the advancement carriage in a forward position.

FIG. 5A is a diagram showing a cross-sectional view of the IOL insertion apparatus 100 with the advancement carriage 202 in a forward position. As described above, the advancement trigger 106 may be used to release the advancement carriage 202 from its proximal position (e.g., proximal position 201 illustrated in FIG. 2). After being released, the combination of the spring system 204 and the dampening system 206 of the advancement carriage 202 moves the advancement carriage 202 forward toward the distal tip 112 at a controlled rate. The controlled rate may be determined in part by the dampening system 206. Forward motion (i.e., movement towards the distal tip 112) of the advancement carriage 202 causes the advancement plunger 208 to move the IOL 212 through the folding chamber 214 and into the deployment chamber 216. In some implementations, the advancement carriage 202 stops at a distal position 501. In some examples, the advancement carriage 202 may be physically prevented from moving any further distally after it reaches the distal position 501. For example, this may be done with structure that physically interferes with and blocks further distal movement of the advancement carriage 202. In some examples, the advancement carriage 202 may abut against and be prevented from moving further by the deployment carriage 222. In other words, in some implementations, the distal position may 501 correspond to the location at which the advancement carriage 202 engages or abuts against the deployment carriage 222.

Figure 5B:
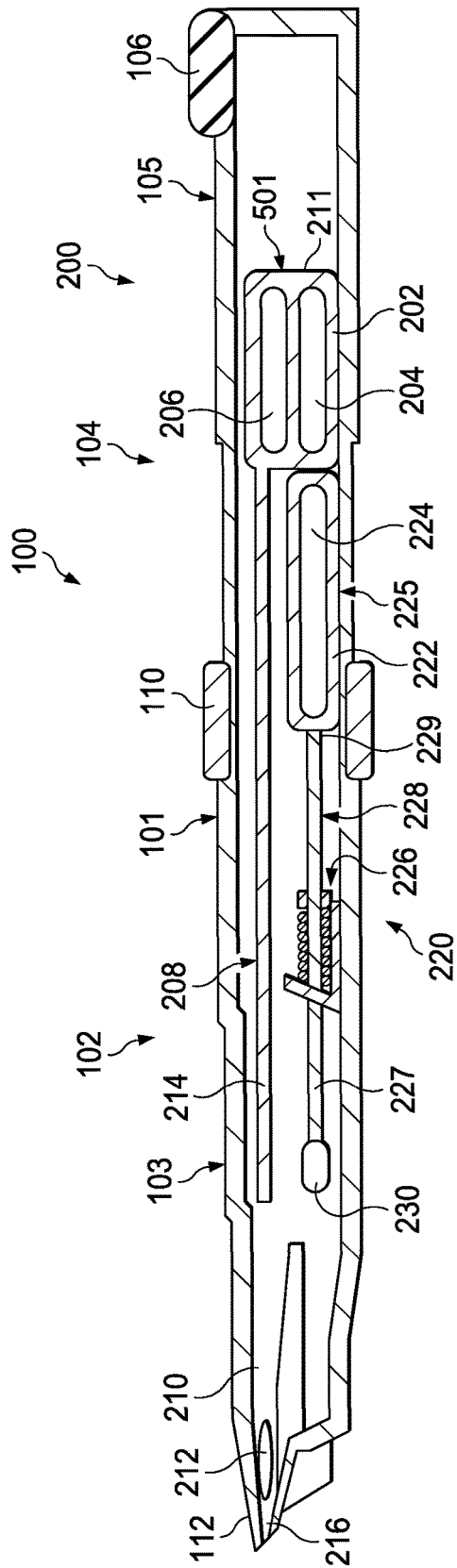
FIG. 5B is a diagram showing a cross-sectional view of the IOL insertion apparatus with the proximal section longitudinally displaced from the distal section.

FIG. 5B is a diagram showing a cross-sectional view of the IOL insertion apparatus with the proximal section 104 longitudinally displaced from the distal section 102. After the advancement carriage 202 has been moved to the distal position 501, an operator may release the proximal section 104 from the distal section 102 with the use of the release tabs 110. The proximal section 104 may then be moved away from the distal section 102. In some examples, as will be described in further detail below, a guidance track may be used to guide the proximal section 104 as it is moved away from the distal section 102.

Figure 6A:
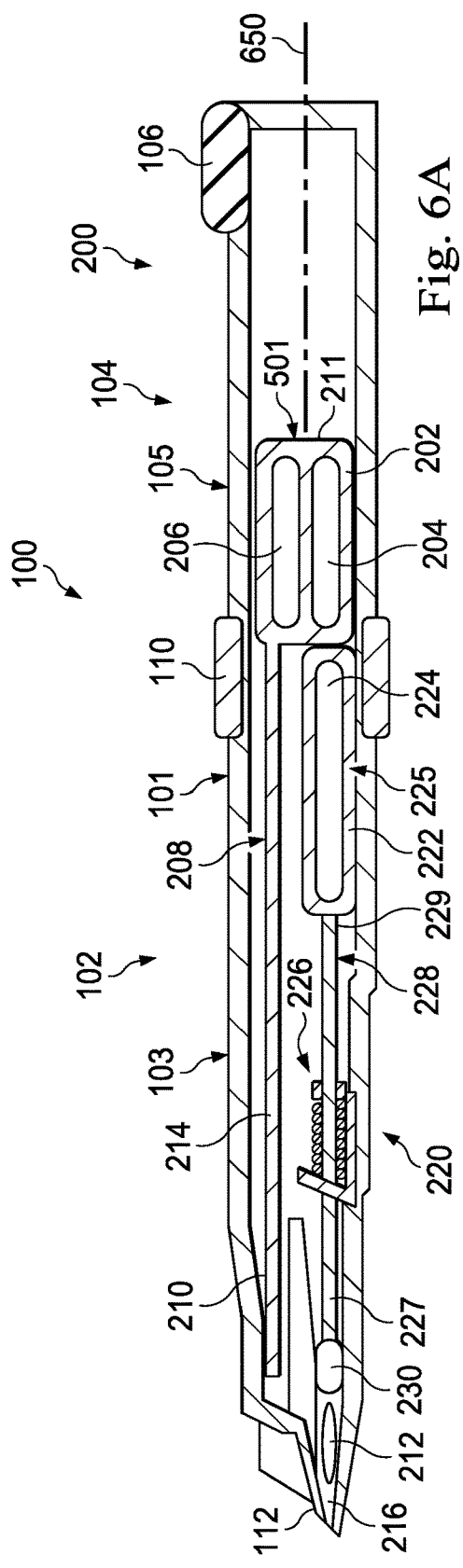
FIG. 6A is a diagram showing a cross-sectional view of the IOL insertion apparatus with a deployment plunger engaged with the IOL and a deployment carriage in a rearward position.

FIG. 6A is a diagram showing a cross-sectional view of the IOL insertion apparatus 100 with the deployment plunger 228 engaged with the IOL 212. In this implementation, the distal section 102 with the IOL 212 has been rotated 180 degrees about a longitudinal axis 650 relative to the proximal section 104 so that the deployment plunger 228, and not the advancement plunger 208, is aligned with and ready to engage the IOL 212. In some examples, the distal section 102 is released from the proximal section 104 through use of the release tabs 110. In some examples, the release tabs 110 are physically prevented from releasing the proximal section 104 from the distal section 102 until the advancement carriage 202 has moved into the distal position 501. This may ensure that the IOL 212 is moved into an appropriate position within the deployment chamber 216 before the advancement plunger 208 is removed from engagement with the IOL 212 and the deployment plunger 228 is engaged with the IOL 212.

In some examples, an operator of the IOL insertion apparatus 100 may axially displace the proximal section 104 away from the distal section 102 after pressing the release tabs 110. The proximal section 104 may be slidingly engaged with the distal section 102 such that as the operator may move the proximal section 104 from the distal section 102, a region of the proximal body 105 slides along a region of the distal body 103. The operator may move the proximal section 104 at least a predefined distance away from the distal section 102 such that the advancement plunger 208, which is carried by the proximal section 104, is fully removed from the folding chamber 214, as shown in FIG. 5B. The operator may then rotate the proximal section 104 relative to the distal section 102 to align the deployment plunger 228 with the IOL 212. In some examples, the proximal section 104 is rotated about 180 degrees relative to the distal section 102. The operator may then move the proximal section 104 axially towards the distal section 102 to a location where the proximal section 104 reconnects with the distal section 102. This will cause the tip 230 of the deployment plunger 228 to pass through the folding chamber and engage the IOL 212 positioned within the deployment chamber 216.

To aid the operator with moving and rotating the proximal section 104 with respect to the distal section 102, the proximal body 105 and the distal body 103 may include guidance features, such as, for example and without limitation, a track. For example, the distal body 103 may include a track while the proximal body 105 may include a protrusion that fits within the track. Conversely, the proximal body 105 may include a track while the distal body 103 may include a protrusion. Other arrangements are also contemplated.

In some implementations, after the proximal section 104 has been rotated relative to the distal section 102 and the deployment plunger 228 has engaged the IOL 212, the deployment trigger 226 may be accessible to an operator. In some examples, while the advancement plunger 208 is aligned with the IOL 212, a portion of the proximal body 105 may cover the deployment trigger 226 so that the deployment trigger 226 is not seen or able to be pressed by the operator. This prevents the operator from inadvertently triggering the deployment process before the deployment plunger 228 is aligned with the IOL 212. In other implementations, the deployment trigger 226 is always accessible to an operator.

Figure 6B:
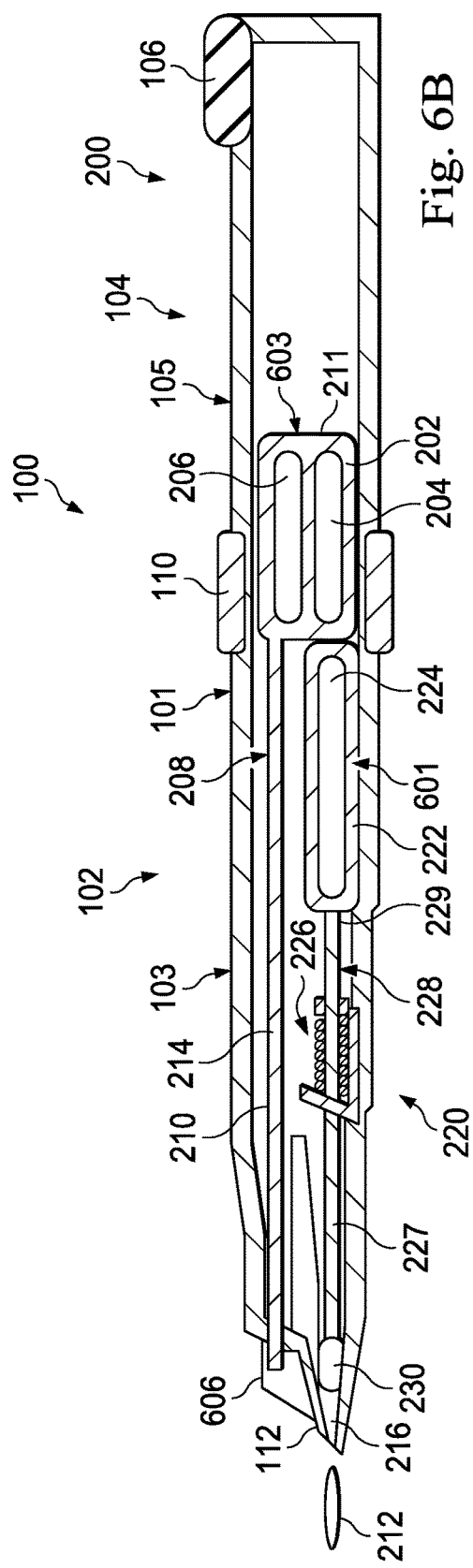
FIG. 6B is a diagram showing a cross-sectional view of the IOL insertion apparatus with the deployment carriage in a forward position.

FIG. 6B is a diagram showing a cross-sectional view of the IOL insertion apparatus 100 with the deployment carriage 222 in a forward position. That is, FIG. 6B shows the deployment carriage 222 in a final distal position 601 after having been distally displaced from an initial position of the deployment carriage 222. According to the present example, when the operator presses the deployment trigger 226, the deployment carriage 222 may be released to advance toward the distal tip 112. The spring system 224 of the deployment carriage 222, which may be biased toward the distal position, causes the deployment carriage 222 to move in the distal direction. This causes corresponding movement of the deployment plunger 228 to engage and push the IOL 212 out of the deployment chamber 216.

In some examples, the advancement carriage 202 may also apply additional force to move the deployment plunger 228 forward. As described above, the advancement carriage 202 may be prevented from moving further when it engages or abuts against the deployment carriage 222. Thus, when the deployment carriage 222 is allowed to move forward, the spring system 204 of the advancement carriage 202 may also move the advancement carriage 202 forward, thereby helping move the deployment plunger 228 forward. The combined force provided by both the spring system 224 of the deployment carriage 222 and the spring system 204 of the advancement carriage 202 may provide a sufficient amount of force to move the tip 230 of the deployment plunger 228 through the narrowing region of the deployment chamber 216. As described above, in some implementations, the tip 230 may be made of a compressible material that compresses and/or conforms to a shape of the deployment chamber 216 as the tip 230 passes therethrough.

Eventually, the deployment carriage 222 reaches its final distal position 601 and the advancement carriage 202 reaches its final distal position 603. With the advancement carriage 202 at its final distal position 603, the distal end 210 of the advancement plunger 208 may be located within a forward chamber 606. The forward chamber 606 may be sized and shaped to receive the distal end 210 of the advancement plunger 208.

In some examples, the deployment trigger 226 is designed such that in an unengaged state, the deployment trigger 226 grips the deployment plunger 228 to prevent distal movement of the deployment plunger 228. However, when the deployment trigger 226 is engaged, the deployment plunger 228 is released and allowed to move forward.

Figure 7A:
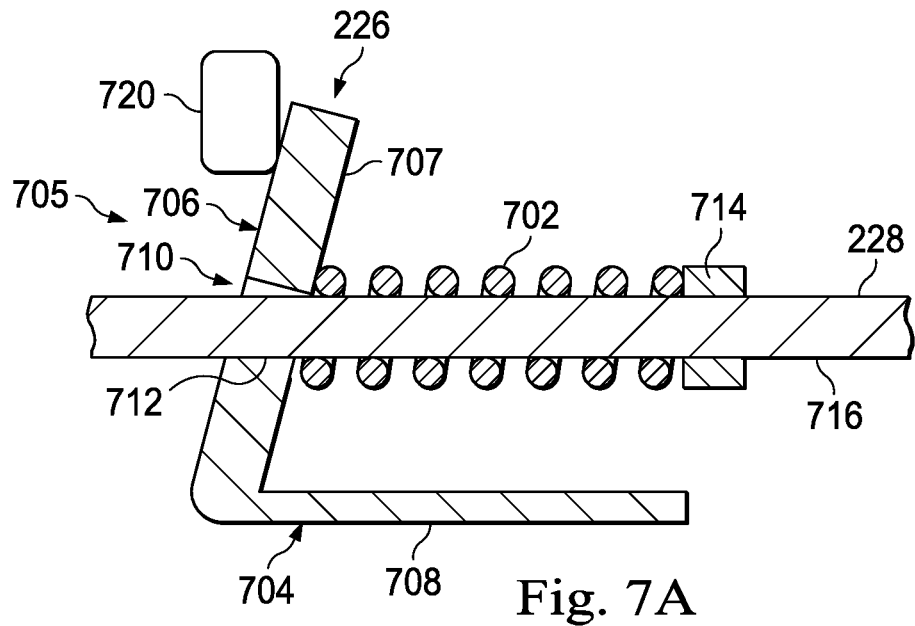
FIG. 7A is a diagram showing an illustrative deployment trigger in an unengaged state.
Figure 7B:
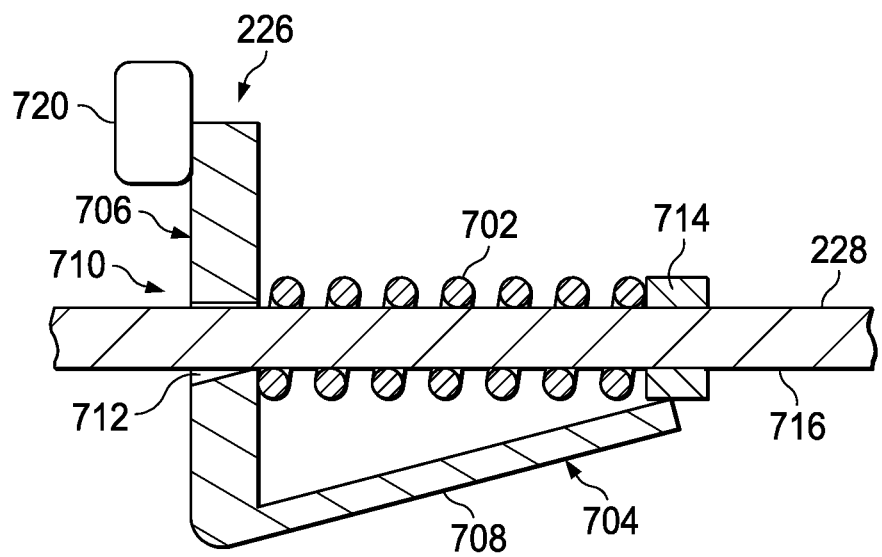
FIG. 7B is a diagram showing the deployment trigger in an engaged state.

FIG. 7A is a diagram showing an illustrative deployment trigger 226 in an unengaged state and a portion of the deployment plunger 228. FIG. 7B is a diagram showing the deployment trigger 226 in an engaged state with the portion of the deployment plunger 228. According to the present example, the deployment trigger 226 comprises a spring-loaded cleat 705. The cleat 705 includes a first portion 706 and a second portion 704. In this implementation, the first portion 706 is angled substantially transverse to the second portion 704.

The cleat 705 is spring-loaded in the distal direction such that the end portion 707 of the first portion 706 is pressed against a hard stop 720. The hard stop 720 thus acts as a pivot point for the cleat 705. When the deployment trigger 226 is not engaged, the cleat 705 is in a locked state as shown in FIG. 7A. Conversely, when the deployment trigger 226 is engaged, by an operator for example, the cleat 705 is in an unlocked state as shown in FIG. 7B.

The first portion 706 includes a tapered through-hole 710 sized and shaped to allow the deployment plunger 228 to pass therethrough. The through-hole 710 includes a gripping surface 712 forming an interior surface of the through-hole 710. Selective contact between the gripping surface 712 and the deployment plunger 228 allows the operator to permit or prevent advancement of the deployment plunger 228 relative to the cleat 705. In the implementation shown, the gripping surface 712 is substantially aligned with an outer surface 716 of the deployment plunger 228 when the deployment trigger 226 is the unengaged state. This maximizes the contact area between the gripping surface 712 and the outer surface 716 of the deployment plunger 228. Thus, when the deployment trigger 228 is not engaged, the cleat 705 grasps the surface 716 of the deployment plunger 228 to prevent distal movement of the deployment plunger 228. In other words, when in the trigger 228 is in the unengaged state, the cleat 705 locks the deployment plunger 228 in place.

A compression spring 702 may bias the cleat 705 to the locked position shown in FIG. 7A. In this implementation, the compression spring 702 extends between the first portion 706 of the cleat 705 and a stop surface 714. The stop surface 714 may be secured to the interior of the handpiece body (e.g., handpiece body 101 shown in FIG. 1).

In this implementation, the second portion 704 includes an actuation surface 708. In some implementations, the actuation surface 708 may be ergonomically designed for an operator's thumb or finger to depress or otherwise move. Pressing the actuation surface 708 causes the cleat 705 to rotate about the hard stop 720 to change the angle of the through-hole 710 relative to the deployment plunger 228 such that the gripping surface 712 no longer fully grips the surface 716 of the deployment plunger 228. Pressing the actuation surface 708 causes the compression spring 702 to compress. Pivoting the cleat 705 as a result of pressing the actuation surface 708 releases the deployment plunger 228 to be moved distally by the spring systems 204, 224 of the advancement carriage 202 and the deployment carriage 222. In other words, the cleat 705 is no longer locked with the deployment plunger 228.

In some implementations, the operator may release the deployment trigger 226 any time during forward motion of the deployment plunger 228 before the deployment carriage 222 reaches its final distal position 601. This allows the compression spring 702 to return the cleat 705 from the unlocked state of FIG. 7B to the locked state of FIG. 7A. By doing this, the user is able to interrupt the automated deployment process by simply releasing the deployment trigger 226. The operator may continue the automated deployment process by re-pressing the deployment trigger 226.

Figure 8:
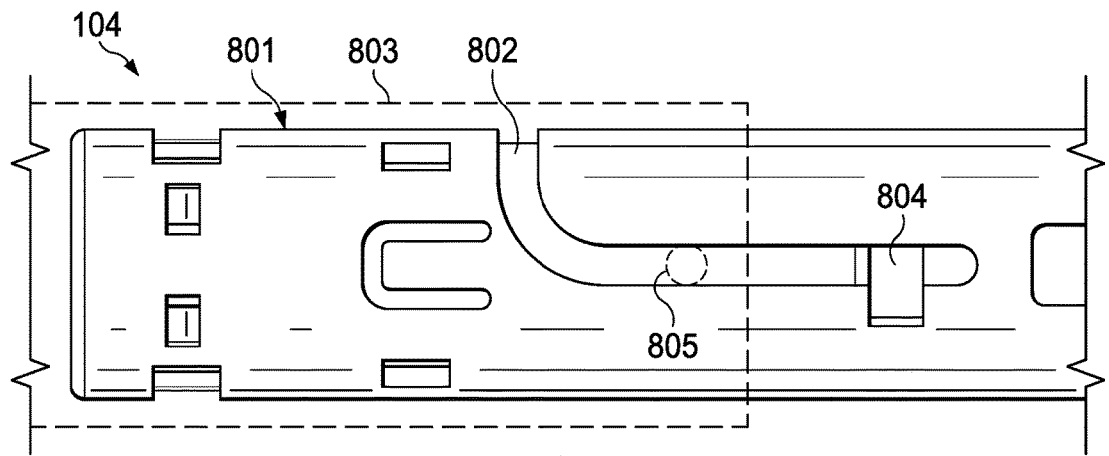
FIG. 8 illustrates a side view of a guidance track formed in a proximal section of an IOL insertion apparatus.

FIG. 8 illustrates a side-view of a guidance track 802 formed in the proximal section 104 of the IOL insertion apparatus 100, according to some implementations. FIG. 8 illustrates an example in which the distal end 801 of the proximal body 105, shown in FIG. 1, includes a guidance track 802. The distal end 801 may be generally covered by a proximal end 803 of the distal body 103, shown in FIG. 1, when the IOL insertion apparatus 100 is fully assembled. Thus, the guidance track 802 is generally not visible to an operator of the assembled IOL insertion apparatus 100. The distal body 103 may include a pin 805 that fits within the guidance track 802. In some instances, the pin 805 may be formed in the proximal end 803 of the distal body 105. The guidance track 802 guides the pin 805 and thus the proximal section 104 as the proximal section 104 is moved and rotated relative to the distal section 102, as shown in FIG. 1. In some implementations, the guidance track 802 may be substantially U-shaped and positioned along the proximal body 105 in a manner such that parallel portions of the U-shaped guidance track 802 extend longitudinally along the IOL insertion apparatus 100.

Figure 9:
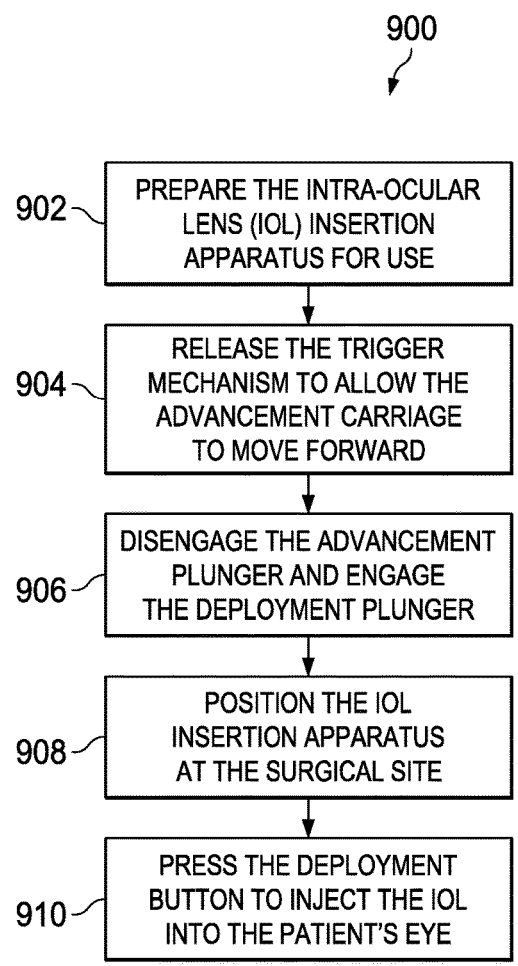
FIG. 9 is a flowchart showing an illustrative method for using an IOL insertion apparatus that provides automated advancement and deployment of the IOL.

FIG. 9 is a flowchart showing an illustrative method for using the IOL insertion apparatus that provides automated advancement and deployment of the IOL. According to the present example, the method 900 includes a step 902 for preparing the IOL insertion apparatus, such as IOL insertion apparatus 100, for use. Preparing the IOL for use may involve removing an IOL lockout mechanism (not shown) and injecting a lubricant, such as a viscoelastic material, into the handpiece body.

In some implementations, the IOL insertion apparatus may come packaged with the IOL disposed within the handpiece body outside the folding chamber in an unfolded state. The IOL lockout mechanism may be a mechanical element attached to the exterior of the handpiece body (e.g., handpiece body 101 shown in FIG. 1). When attached to the handpiece body, the IOL lockout mechanism may mechanically secure the IOL in place to prevent unwanted movement during shipping. The IOL lockout mechanism may also mechanically block forward motion of an advancement carriage to avoid premature triggering of the advancement process.

After the IOL lockout mechanism has been removed, the operator may inject a lubricant into the folding chamber. The lubricant may fill space around the IOL to provide lubrication for the IOL as it passes through the folding chamber. In some implementations, the lubricant may be an Ophthalmic Visio-surgical Device (OVD) fluid.

At 904, the method 900 may include releasing an advancement trigger mechanism to allow the advancement carriage to move forward. As described above, the operator may press a button that mechanically releases the advancement carriage. Because the advancement carriage is spring biased in the distal direction, the advancement carriage moves from a first, proximal position to a second, distal position within the handpiece body. Because the advancement carriage is attached to the advancement plunger, forward motion of the advancement carriage causes forward motion of the advancement plunger, which moves the IOL out of its original placement and through the folding chamber. Passage of the IOL through the folding chamber causes it to be folded as desired before it is inserted into the patient's eye.

At 906, the method 900 may include disengaging the advancement plunger from the IOL and engaging the deployment plunger with the IOL. This may be done, for example, by pulling, rotating, and pushing the proximal section of the IOL insertion apparatus relative to the distal section of the IOL insertion apparatus as described above.

At 908, the method 900 may include positioning the IOL insertion apparatus at the surgical site. In some examples, a small incision is made in the patient's eye at the surgical site. In some examples, the incision may be less than 2 millimeters. Placement of the IOL insertion apparatus may involve placing the distal tip (such as distal tip 112 shown in FIG. 1) through the incision so that when the IOL is moved out of the distal tip, it is passed through the incision.

At 910, the method 900 may include pressing the deployment trigger to inject the IOL into the patient's eye. As described above, pressing the deployment trigger may release the deployment plunger and may allow the spring system of the deployment carriage to move the deployment plunger forward. Forward motion of the deployment plunger may advance the IOL out of the distal tip of the IOL insertion apparatus, through the incision, and into the patient's eye.

Use of methods and systems described herein provides a number of benefits and advantages. For example, because deployment of the IOL is automated rather than relying on manual human operation, there may be less risk that the IOL will be deployed improperly. Furthermore, while automated, deployment of the IOL as described herein does not rely on external power or external connection. Instead, automated deployment of the IOL may be accomplished mechanically through the spring systems described herein. Thus, the IOL insertion apparatus may be a self-contained device that is able to operate without being connected to any external machine.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intraocular lens (IOL) insertion apparatus comprising:
   a handpiece body having a distal tip, wherein the handpiece body comprises a distal section and a proximal section, the proximal section being slidingly engaged and rotatable from a first rotational position to a second rotational position relative to the distal section when proximally displaced from the distal section;
   a deployment chamber located at a distal end of the handpiece body, the deployment chamber sized and shaped to hold a folded IOL;
   a deployment system disposed within the handpiece body, the deployment system comprising:
      a deployment carriage movable between a first position and a second position within the handpiece body, the deployment carriage including a biasing element that biases the deployment carriage in a distal direction toward the distal tip;
      a deployment trigger that prevents distal movement of the deployment carriage unless pressed; and
      a deployment plunger having a proximal end secured to the deployment carriage and a distal end to engage the folded IOL.

2. The apparatus of claim 1, further comprising, an advancement system disposed within the handpiece body, the advancement system comprising:
   an advancement carriage located within the handpiece body at a location proximal of the deployment carriage, the advancement carriage including a biasing element biasing the advancement carriage in the distal direction toward the deployment carriage and including a dampening system to dampen motion of the advancement carriage; and
   an elongated advancement plunger having a distal end arranged to engage the IOL and a proximal end connected to the advancement carriage.

3. The apparatus of claim 2, wherein the advancement carriage is operative to abut against the deployment carriage after moving in the distal direction.

4. The apparatus of claim 3, wherein the biasing element of the advancement carriage and the biasing element of the deployment carriage together provide a force to push the IOL out of the distal tip.

5. The apparatus of claim 2, further comprising an advancement trigger to release the advancement carriage to move in the distal direction.

6. The apparatus of claim 1, wherein the deployment trigger comprises a spring-loaded cleat.

7. The apparatus of claim 6, wherein the cleat comprises a through-hole, the deployment plunger extending through the through-hole.

8. The apparatus of claim 7, wherein when the deployment trigger is in an unengaged state, the cleat grasps the deployment plunger with a surface of the through-hole to prevent distal movement of the deployment carriage.

9. The apparatus of claim 8, wherein engagement of the deployment trigger changes an angle of the through-hole to allow the deployment plunger to slide through the through-hole.

10. The apparatus of claim 1, wherein when the proximal section is at the first rotational position relative to the distal section, an advancement plunger is aligned with the IOL, and when the proximal section is at the second rotational position relative to the distal section, the deployment plunger is aligned with the IOL.

11. The apparatus of claim 10, wherein the deployment trigger is inaccessible to an operator until the proximal section is at the second rotational position with respect to the distal section.

12. The apparatus of claim 1, wherein the biasing element of the deployment carriage comprises a constant force spring.

13. An intraocular lens (IOL) insertion apparatus comprising:
   a handpiece body having a proximal section and a distal section, the distal section having a distal tip, the distal section being rotatable relative to the proximal section between a first rotational position and a second rotational position, the first rotational position aligning an advancement plunger with an IOL positioned within the handpiece body, and the second rotational position aligning a deployment plunger with the IOL;
   a deployment carriage connected to a proximal end of the deployment plunger and releasably secured at a first position within the handpiece body by a deployment trigger, the deployment carriage comprising a first biasing element that biases the deployment carriage in a distal direction toward the distal tip; and
   an advancement carriage connected to a proximal end of the advancement plunger and releasably secured within the handpiece body by an advancement trigger mechanism, the advancement carriage comprising a second biasing element to bias the advancement carriage in the distal direction.

14. The apparatus of claim 13, wherein the advancement carriage is operative to abut against the deployment carriage after moving in the distal direction.

15. The apparatus of claim 13, wherein the deployment trigger grips the deployment plunger to prevent distal movement of the deployment carriage, and when pressed, allows the deployment plunger to move in the distal direction.

16. The apparatus of claim 15, wherein the deployment trigger is inaccessible until the distal section is at the second rotational position relative to the proximal section.

17. A method comprising:
   positioning a distal end of an intraocular lens (IOL) insertion apparatus handpiece at a surgical site;
   triggering an advancement trigger mechanism that releases an advancement carriage, the advancement carriage having an advancement plunger extending from a distal end, the advancement carriage being biased in a distal direction such that when released, the advancement carriage moves a distal tip of the advancement plunger through a folding chamber to fold an IOL engaged with the distal tip; and
   rotating a proximal section of the handpiece with respect to a distal section of the handpiece to align a deployment plunger with the folded IOL; and
   actuating a deployment trigger to release a deployment carriage, the deployment carriage having the deployment plunger extending from a distal end, the deployment carriage being biased in the distal direction such that when the deployment trigger is actuated, the deployment carriage causes the deployment plunger to move the folded IOL out of the IOL insertion apparatus.

18. The method of claim 17, further comprising:
   before rotating the proximal section, moving the proximal section away from the distal section; and
   after rotating the proximal section, moving the proximal section towards the distal section.

19. The method of claim 17, further comprising, releasing the deployment trigger during distal movement of the deployment carriage to interrupt the distal movement of the deployment carriage.

\* \* \* \* \*